(12) United States Patent
Giannuzzi et al.

(10) Patent No.: US 6,603,119 B1
(45) Date of Patent: Aug. 5, 2003

(54) CALIBRATION METHOD FOR QUANTITATIVE ELEMENTAL ANALYSIS

(75) Inventors: Lucille A. Giannuzzi, Winter Park, FL (US); Frederick A. Stevie, Orlando, FL (US); Catherine Vartuli, Windermere, FL (US)

(73) Assignee: Agere Systems Inc., Allentown, PA (US)

(*) Notice: Subject to any disclaimer, the term of this patent is extended or adjusted under 35 U.S.C. 154(b) by 0 days.

(21) Appl. No.: 09/567,675

(22) Filed: May 9, 2000

(51) Int. Cl.[7] .................................................. H01J 49/26
(52) U.S. Cl. ....................... 250/299; 250/282; 250/252.1
(58) Field of Search .................................. 250/299, 282, 250/281, 252.1, 252 R

(56) References Cited

U.S. PATENT DOCUMENTS

| | | |
|---|---|---|
| 4,575,869 A | 3/1986 | Torrisi et al. |
| 4,697,080 A | 9/1987 | King |
| 5,077,469 A | 12/1991 | Fabinski et al. |
| 5,210,778 A | 5/1993 | Massart |
| 5,350,919 A * | 9/1994 | Hirano et al. ............ 250/252.1 |
| 5,390,230 A | 2/1995 | Chang |
| 5,459,677 A | 10/1995 | Kowalski et al. |
| 5,475,234 A | 12/1995 | Xu et al. |
| 5,550,372 A * | 8/1996 | Yasue .......................... 250/307 |
| 5,650,616 A * | 7/1997 | Iketaki ....................... 250/288 |
| 5,866,899 A | 2/1999 | Hossain |
| 5,933,792 A | 8/1999 | Andersen et al. |
| 6,035,246 A | 3/2000 | Wagner |
| 6,040,198 A | 3/2000 | Komiya et al. |
| 6,043,486 A * | 3/2000 | Hossain ................... 250/252.1 |

* cited by examiner

Primary Examiner—John R. Lee
Assistant Examiner—Zia R. Hashmi

(57) ABSTRACT

The present invention provides a method of calibrating an analytical tool. The method, in a illustrative embodiment, includes preparing a calibration standard having a known concentration of an element and obtaining a portion of the calibration standard with a focused beam, wherein the calibration standard is representative of the concentration. The portion of the calibration standard is then used to calibrate an analytical tool.

23 Claims, 7 Drawing Sheets

CALIBRATION METHOD FOR QUANTITATIVE ELEMENTAL ANALYSIS

TECHNICAL FIELD OF THE INVENTION

The present invention is directed, in general, to a method of calibrating an analytical tool and, more specifically, to a method of calibrating an analytical tool including determining a detection limit associated with the tool.

BACKGROUND OF THE INVENTION

In semiconductor processing today, it is often necessary to spectroscopically examine portions of a semiconductor die to determine the results of new or conventional processes. The examination may be to confirm the results of an experimental process, to determine the nature of a particular failure or defect in a semiconductor device, or even to find impurities within the semiconductor device. Of course, because of the nature of integrated circuits, the examination must often be performed on samples cut from the die in question. Scanning electron microscopy/energy dispersive spectroscopy (SEM/EDS) is frequently used in the determination of the composition of target materials in a feature of a semiconductor die. Other analytical tools are also available to examine these samples, for example a few are auger electron spectrometer (AES), secondary ion mass spectrometer (SIMS), and transmission electron microscope (TEM).

Often, a semiconductor die or wafer is taken off the production line and brought to one of the analytical tools discussed above, to look for impurities. This is a very important step in semiconductor manufacturing because certain impurities, in certain concentrations and within specific materials, typically cause semiconductor device failure. Since it is commonly known which impurities are not desired within a specific material, and since the impurity concentration that is unacceptable is also known, the analytical tools can often be of help.

Certain analytical tools are more helpful, when looking for certain impurities in specific concentrations. Currently, certain analytical tools are known for being better suitable for different applications; however, each tool's detection limit, for a given element within a given material, today may only be approximated and not known within an acceptable degree of certainty. This impacts the semiconductor manufacturing industry, in that a person performing a test on a semiconductor wafer cannot say, with great certainty, that even though the element did not register, less than X amount must be present. Moreover, the various detection limits of the different analytical tools are not known with enough certainty, that a given impurity scenario could be allocated to a certain tool.

Accordingly, what is needed in the art is a calibration method for use in analytical inspection tools, that allows the analytical tools to have a detection limit associated therewith depending on the impurity desired, concentration thereof and material located within, that alleviates the problems associated with the prior art.

SUMMARY OF THE INVENTION

To address the above-discussed deficiencies of the prior art, the present invention provides a method of calibrating an analytical tool. The method, in a illustrative embodiment, includes preparing a calibration standard having a known concentration of an element and obtaining a portion of the calibration standard with a focused beam, wherein the calibration standard is representative of the concentration. The portion of the calibration standard is then used to calibrate an analytical tool.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
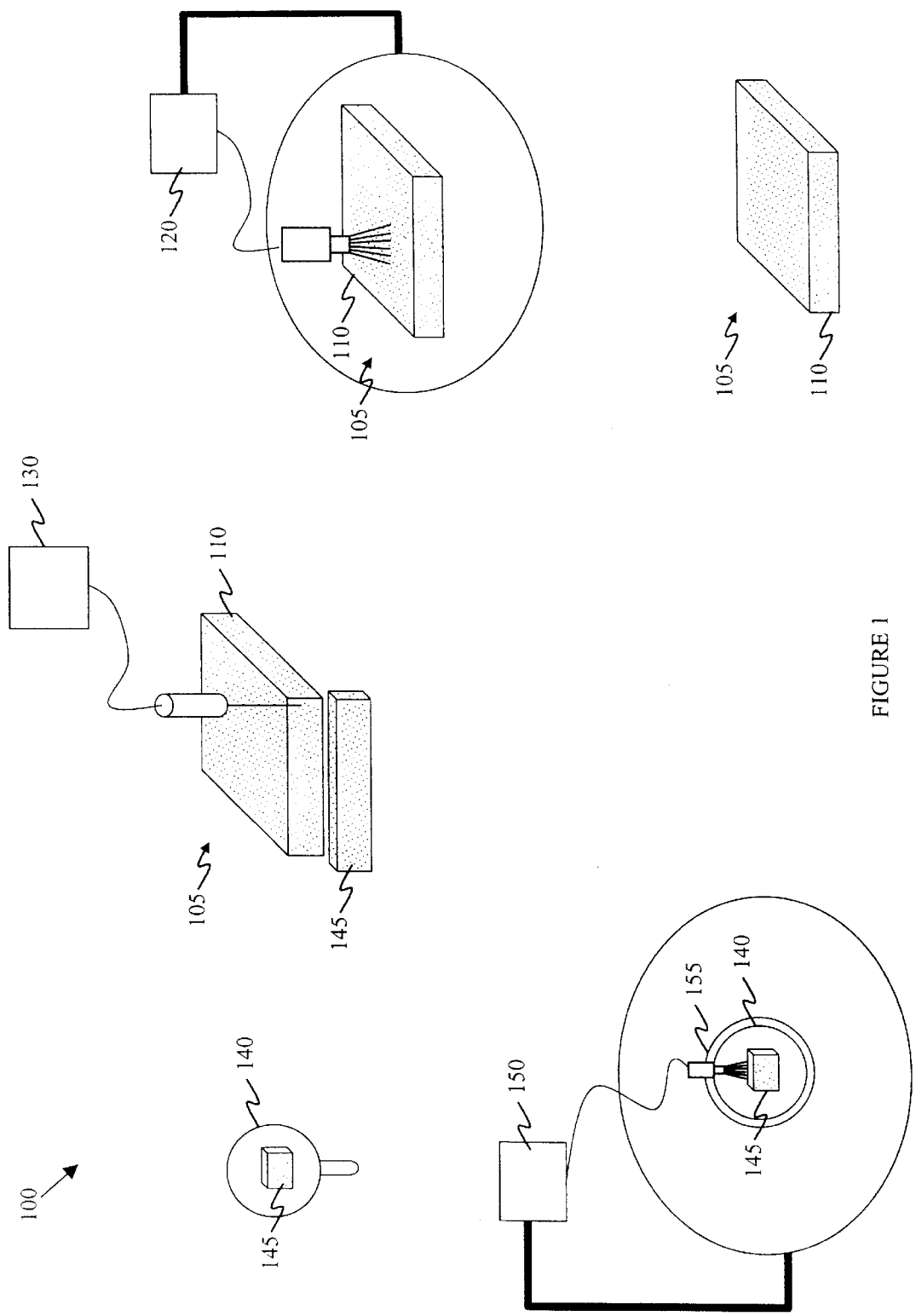
FIG. 1 illustrates a system for calibrating an analytical tool that forms one environment within which the present invention can operate.

Referring initially to FIG. 1, there is illustrated a system for calibrating an analytical tool, generally designated 100, that forms one environment within which the present invention can operate. The system 100 includes a calibration standard 105 that comprises a known matrix 110, such as silicon, having a known concentration of an element located therein. While the calibration standard 105 is typically a relatively large sample, the concentration of the element throughout the calibration standard 105 should preferably be uniform. As used herein, the term "element" may be either an atomic element, such as fluorine, or a compound such as boron difluoride.

Also illustrated in FIG. 1 is a first analytical tool 120 capable of determining the concentration of the calibration standard 105. The first analytical tool 120 is advantageously placed over the calibration standard 105. The first analytical tool 120 then scans the calibration standard 105 to obtain concentration data of the calibration standard 105, which is usually represented in a graph. A secondary ion mass spectrometer (SIMS) is one analytical tool 120 that is well suited for this particular phase of the calibration method. This is a result of its ability to obtain rather accurate data from a sample that has a uniform concentration of an element therein.

The system 100 also includes a focused beam apparatus 130. The focused beam apparatus, in one particularly advantageous embodiment, may be a focused ion beam (FIB) apparatus as set forth in U.S. patent application Ser. No. 09/337,966, filed on Jun. 6, 1999, entitled "Scanning Electron Microscope/Energy Dispersive Spectroscopy Sample Preparation Method and Sample Produced Thereby," which is commonly assigned and co-pending. Furthermore, the focused beam apparatus 130 may, in another embodiment, be a subatomic particle beam apparatus, a laser beam apparatus or any other applicable beam apparatus that can be used to obtain thin portions of the calibration standard 105.

The system 100 may further include a sample holder 140. The sample holder 140 holds a portion of the calibration standard 145 removed from the calibration standard 105 by the focused beam apparatus 130. The sample holder 140 is typically designed to be used in different analytical tools, which makes moving the portion 145 from one tool to another much easier. Furthermore, there is no need to move the portion 145 from one holder to another or make multiple portions 145, which saves significant time in the analytical process.

Figure 2A:
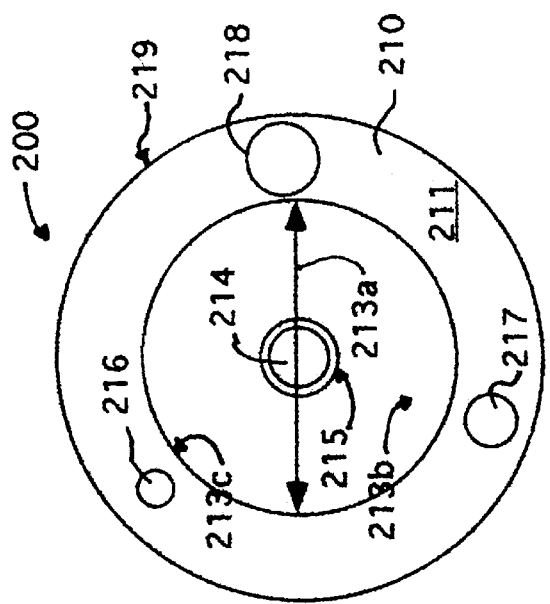
FIGS. 2A–2C illustrate top and bottom views of one particularly advantageous embodiment of a sample holder.
Figure 2B:
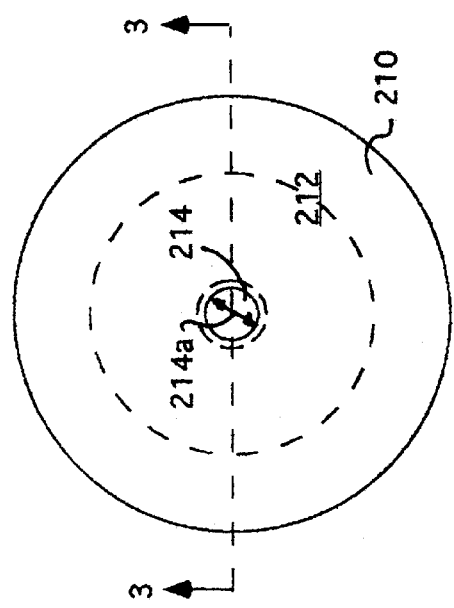
Figure 2C:
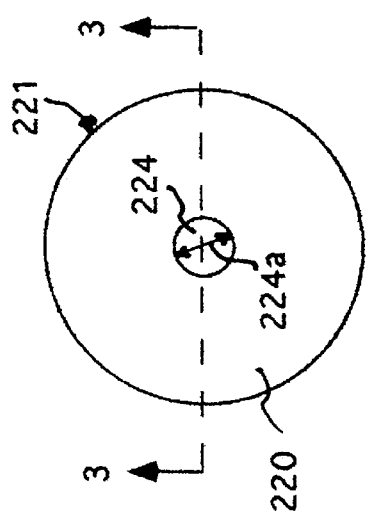

Turning briefly to FIGS. 2A–2C, illustrated are top and bottom views of one particularly advantageous embodiment of the sample holder 140 (FIG. 1). The advantageous embodiment sample holder 200 may be a sample holder as set forth in U.S. patent application Ser. No. 09/320,369, filed on May 25, 1999, entitled "Sample Holder for Multiple Diagnostic Tools and Methods of Manufacture and Operation Thereof," which is commonly assigned and co-pending. The advantageous sample holder 200 comprises a main body 210 and a mating plug 220. The main body 210 has first and second opposing major surfaces 211, 212, a recess 213 in the first major surface 211, and a main body aperture 214 therethrough. The recess 213 has a base 213b wherein the main body aperture 214 extends from the recess base 213b through the main body 210 to the second major surface 212. The main body aperture 214 is smaller in diameter 214a than a diameter 213a of the recess 213. The plug 220 comprises a plug aperture 224 therethrough that, when installed, aligns with the main body aperture 214. An outer surface 221 of the plug 220 is adapted to engage an inner surface 213c of the recess 213.

Returning to FIG. 1, also illustrated is a second analytical tool 150. The second analytical tool 150, for example, may be energy dispersive spectrometry (EDS) used in a scanning electron microscope (SEM), a transmission electron microscope (TEM), or a scanning transmission electron microscope (STEM), microcalorimetry, auger electron spectroscopy (AES), or x-ray photoelectron spectroscopy (XPS). However, one having skill in the art knows that the analytical tool is not limited to one of those provided, and that other analytical tools may be used. Furthermore, as set forth in the illustrated embodiment, the second analytical tool 150 may have a sample holder bay 155 configured to hold the sample holder 140.

Figure 3:
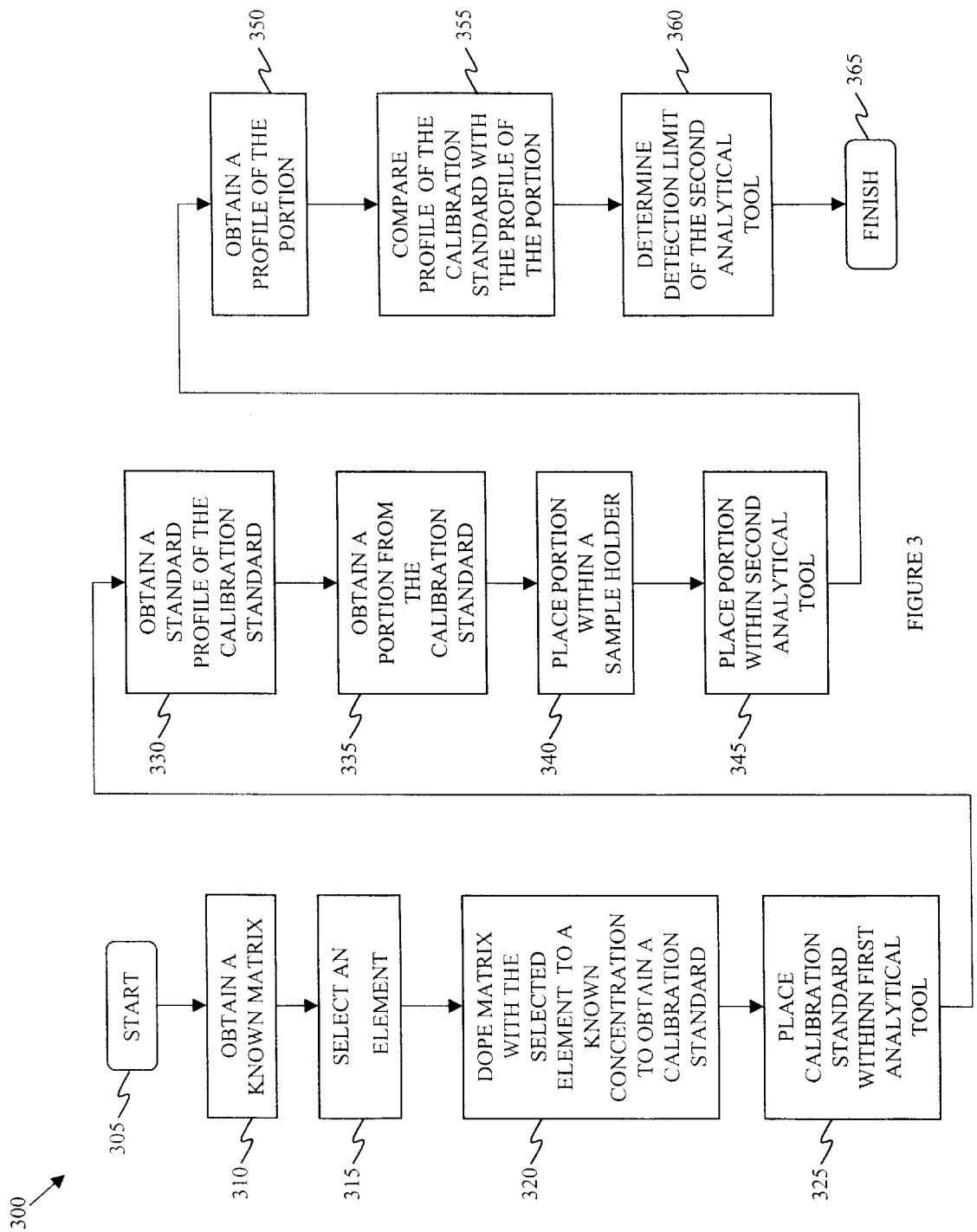
FIG. 3 illustrates a flow diagram of a method of calibrating an analytical tool.

Turning now to FIG. 3 with continued reference to FIG. 1, illustrated is a flow diagram 300 of a method of calibrating an analytical tool. In FIG. 3, the system first performs initialization in step 305. After initialization, in step 310 a known matrix 110 is obtained. The known matrix 110 may be any material, and more specifically, it may be any material typically used in the manufacture of a semiconductor wafer. Examples of such materials are silicon, silicon dioxide, germanium, aluminum, copper, tantalum or tungsten; however, it should be noted that this is not an exhaustive list of possible materials.

In a step 315, a known implanting element, which may be an atomic element or a compound, is selected. Generally, the element that is selected depends on the elements that are to be analyzed. More specifically, these elements will typically be elements that are currently used in the manufacture of semiconductor wafers and integrated circuits. An example of an element presently used in the semiconductor manufacturing industry is fluorine. The selected element, in step 320, is introduced into the matrix 110, to a known concentration; thus, creating the calibration standard 105. One having skill in the art knows the conventional methods by which the element may be introduced into the matrix, including various deposition techniques or ion implantation techniques. As is well known, ion implantation can be used to precisely control the amount of the element introduced into the matrix 110. While the concentration may vary, one embodiment provides a concentration of the known element in the matrix of about 1E21 atoms/cm$^3$. One having skill in the art knows that steps 310, 315, 320 are only required if a matrix having a known element and concentration within, has not previously been manufactured.

Figure 4:
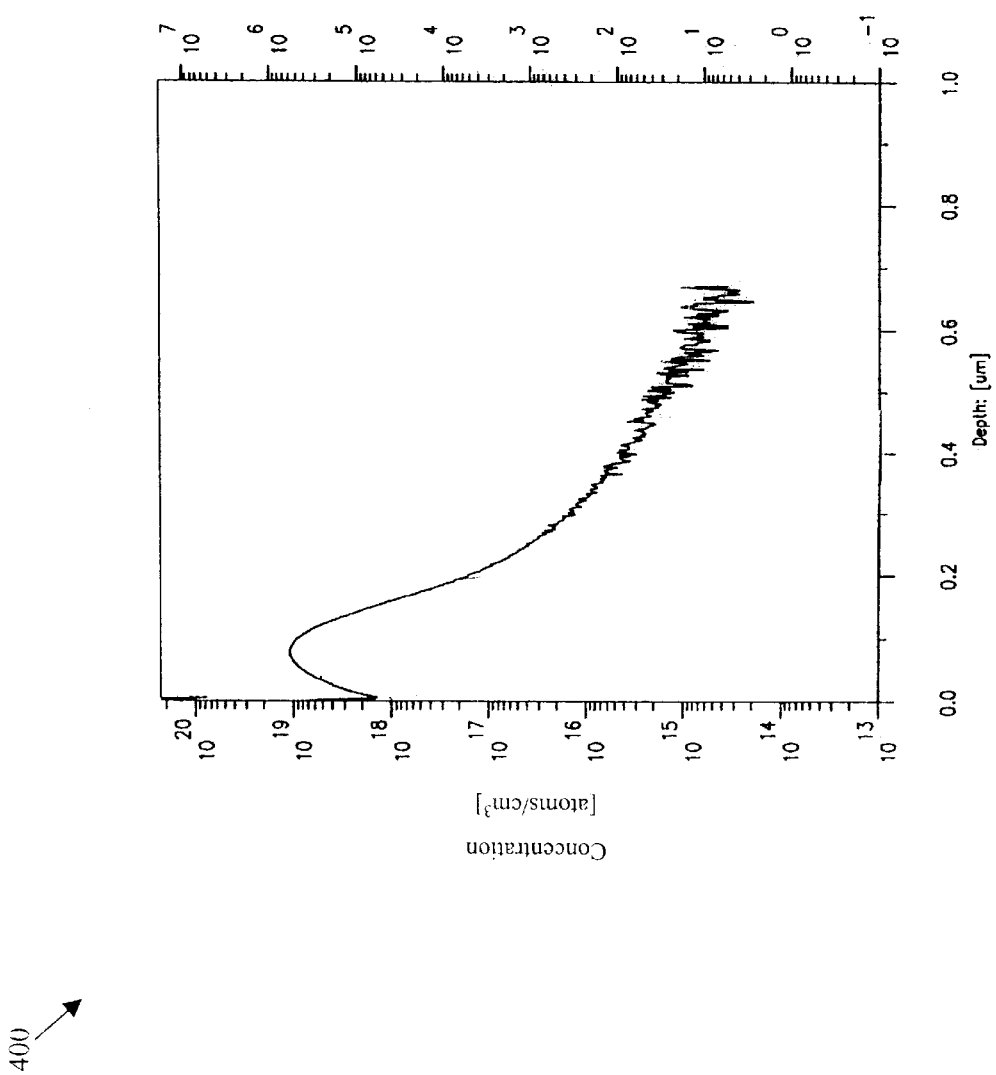
FIG. 4 illustrates a standard SIMS profile of a known calibration standard.

In a step 325, the calibration standard 105 is placed within a first analytical tool 120. The first analytical tool 120, in a illustrative embodiment, is a secondary ion mass spectrometer (SIMS); however, one having skill in the art knows that other, accurate, first analytical tools 120 may be used. The first analytical tool 120 is used to obtain a standard concentration profile of the calibration standard 105, in step 330. Current SIMS technology, and any other technology if deemed suitable, is sufficiently accurate to determine, with a great amount of certainty, what elements are present and to what concentration; thus, providing the SIMS profile illustrated in FIG. 4. Turning briefly to FIG. 4, illustrated is a standard SIMS profile 400 of fluorine.

After determining the standard profile in step 330, the portion of the calibration standard 145, which is representative of the concentration, is obtained in a step 335. As mentioned earlier, a focused beam apparatus 130 is preferably used to obtain the portion 145. In a more illustrative embodiment, the focused beam apparatus 130 may be a focused ion beam apparatus, or in other embodiments a sub-atomic beam apparatus or laser beam apparatus. The focused beam apparatus 130, as stated earlier, is used to obtain the portion 145. Preferably, the portion 145, is removed from a region near the surface of the calibration standard 105, which best represents the element's concentration. However, depending on the uniformity of the concentration within the calibration standard 105, the portion 145 may be removed from different areas.

The portion 145, in a more specific embodiment, is a thin portion having a thickness ranging from about 50 nm to about 5000 nm. Furthermore, the thin portion may have a length of about 20000 nm and a depth of about 5000 nm; however, one skilled in the art knows that various thicknesses, lengths and widths may be obtained by the focused beam apparatus 130.

In an optional step 340, the portion 145 may be placed within a sample holder 140. The sample holder 140 allows the portion 145 to be precisely secured to the second analytical tool 150, as is described in subsequent steps. It should be mentioned that the sample holder 140 is extremely beneficial, but not required, and the method currently discussed could be used without it. For example, most analytical tools have their own sample holder 140. In such instances, the analytical tool's own sample holder could be used if desired.

In a step 345, the portion 145 is placed under the scanning path of a second analytical tool 150. The second analytical tool 150 is the tool that is desired to be calibrated. As mentioned earlier, the second analytical tool 150 may be an energy dispersive spectrometry (EDS) used in a scanning electron microscope (SEM), a transmission electron microscope (TEM), or a scanning transmission electron microscope (STEM), microcalorimetry, auger electron spectroscopy (AES), or x-ray photoelectron spectroscopy (XPS); however, the illustrated method of calibration may be used to calibrate analytical tools other than those just described.

Figure 5:
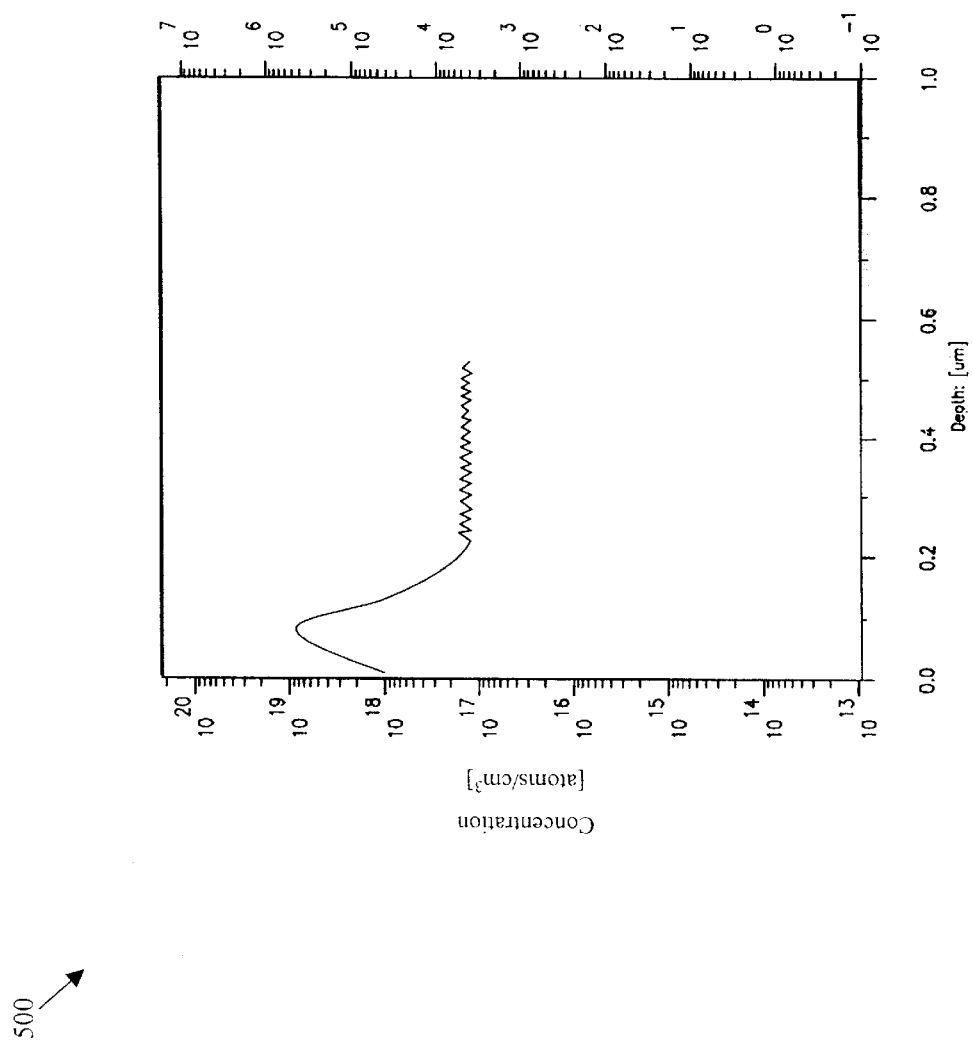
FIG. 5 illustrates a conventional profile of a portion of a calibration standard provided by a second analytical tool.
Figure 6:
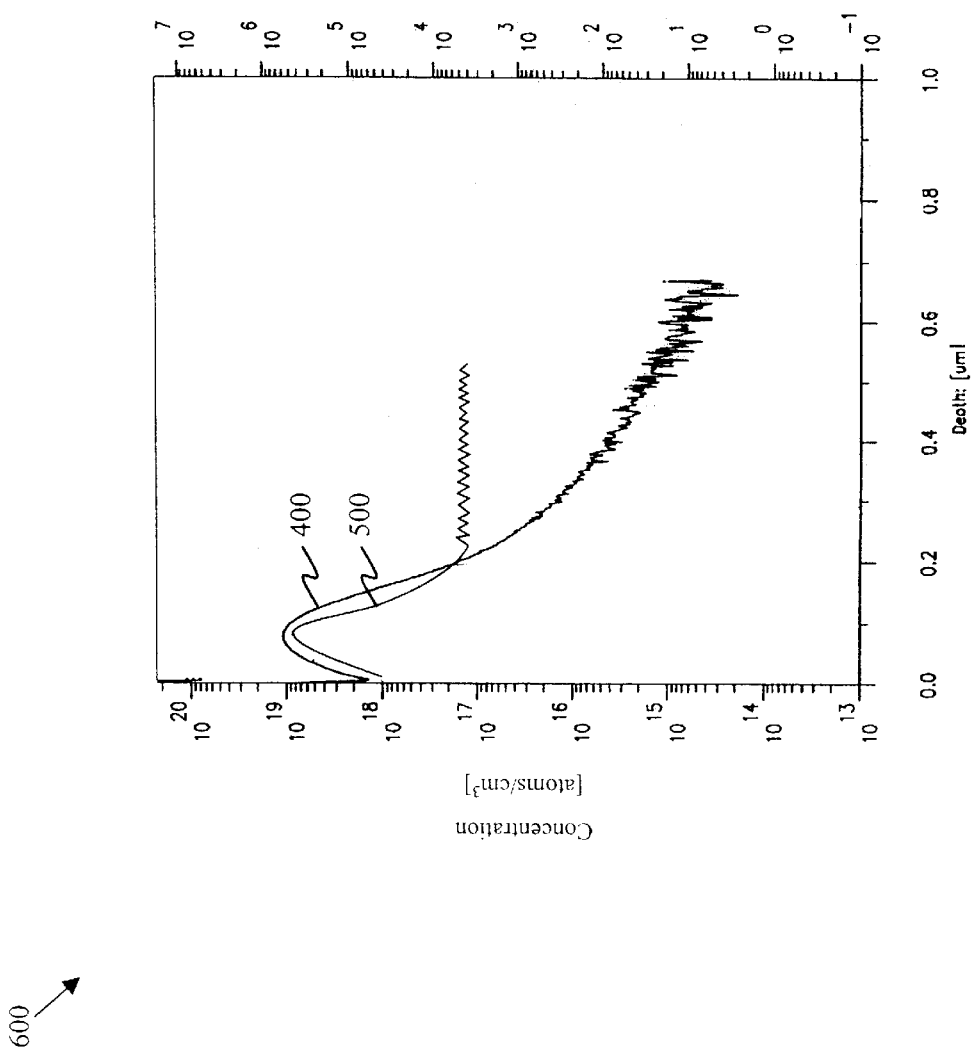
FIG. 6 illustrates a graph representing the comparison of the profiles illustrated in FIGS. 4 and 5.

After the portion 145 is placed within the second analytical tool 150, a profile of the portion 145 is obtained, in a step 350. Turning briefly to FIG. 5, illustrated is a profile 500 provided by the second analytical tool 150. The profile 500 is a graphical representation of the concentration of fluorine in the portion 145. Once the profile 500 is obtained, this profile 500 is compared with the standard profile 400. From this comparison, a profile 600 is obtained in step 355, as illustrated in FIG. 6. If the second analytical tool 150 is calibrated properly, the peak concentration level of the portion 145, represented by profile 500, should correspond closely to the peak concentration level of the calibration standard 105, represented by profile 400, as seen from the comparison profile 600. As illustrated, the peak concentration of the profile 500 is just below that of the profile 400, and as such, the second analytical tool 150 is adjusted or calibrated to reflect the correct concentration.

Figure 7:
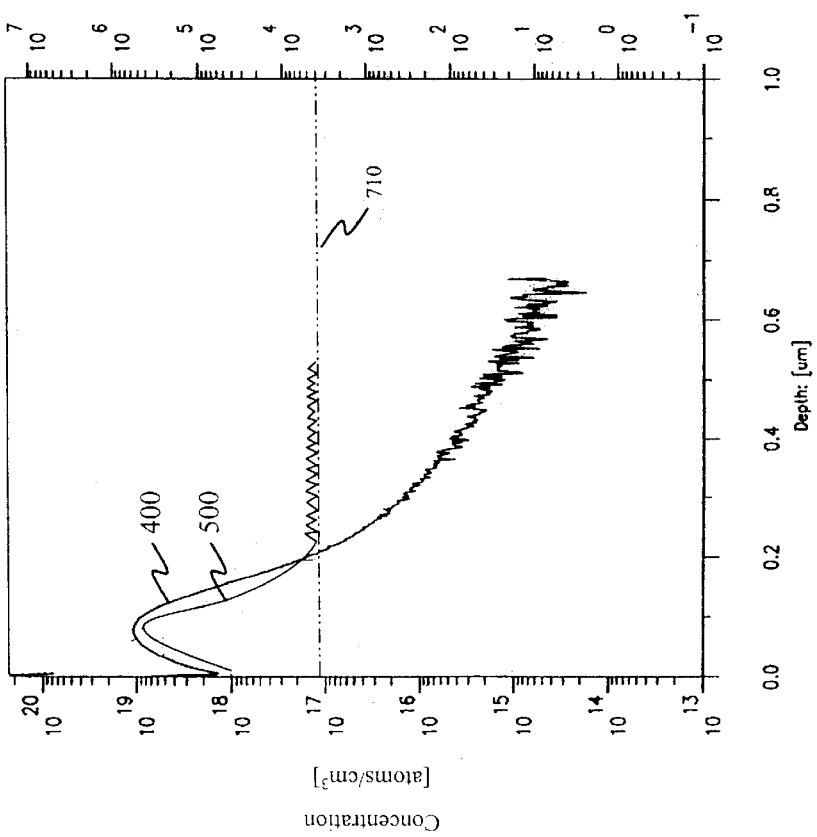
FIG. 7 illustrates the graph of FIG. 6, further showing the detection limit of the second analytical tool.

The comparison profile 600 can also be used to determine a detection limit of the second analytical tool 150 as indicated in step 360. The concentration detection limit is the limit below which the second analytical tool 150 cannot accurately read the element's concentration. As can be seen in FIG. 7, the first analytical tool 120 can detect concentrations of fluorine ranging from about 1E16 atoms/cm$^3$ to about 1E15 atoms/cm$^3$ as represented by profile 400. However, as can also be seen, the second analytical tool 150 can only detect concentrations of fluorine down to about 1E17 atoms/cm$^3$, as represented by profile 500. Therefore, the detection limit of this particular second analytical tool 150 for the given element concentration and matrix is illustrated by line 710 and is about 1E17 atoms/cm$^3$.

After obtaining the detection limit of the second analytical tool 150 the process is completed in a finish step 365. It is readily apparent that the above process may be repeated to calibrate and determine the detection limits of as many second analytical tools as desired, using the same portion 145, or a different portion 145, having a different element and located within different matrices.

Although the present invention has been described in detail, those skilled in the art should understand that they can make various changes, substitutions and alterations herein without departing from the spirit and scope of the invention in its broadest form.

What is claimed is:

1. A method of calibrating an analytical tool, comprising:
   preparing a calibration standard having a known concentration of an element;
   obtaining a layer of the calibration standard with a focused beam, the layer being representative of the concentration of the element;
   providing an analytical tool; and
   calibrating the analytical tool with the layer.

2. The method as recited in claim 1 further including obtaining a detection limit of the analytical tool with respect to the concentration.

3. The method as recited in claim 1 wherein preparing a calibration standard includes implanting the calibration standard with a known concentration of the element.

4. The method as recited in claim 3 wherein implanting includes implanting the calibration standard with the element to achieve a concentration of about 1E21 atoms/cm$^3$ of the element.

5. The method as recited in claim 3 wherein implanting the element includes implanting the element by ion implantation.

6. The method as recited in claim 1 wherein preparing a calibration standard includes determining the concentration using secondary ion mass spectrometry (SIMS) or rutherford backscattering spectrometry (RBS).

7. The method as recited in claim 1 wherein obtaining a layer of the calibration standard includes obtaining a layer of the calibration standard with a focused ion beam process.

8. The method as recited in claim 1 wherein obtaining a layer of the calibration standard includes obtaining a layer of the calibration standard with a subatomic particle beam or a laser beam.

9. The method as recited in claim 1 wherein calibrating an analytical tool includes calibrating an analytical tool selected from the group consisting of:
   energy dispersive spectrometry (EDS),
   microcalorimetry,
   auger electron spectroscopy (AES), and
   x-ray photoelectron spectroscopy (XPS).

10. The method as recited in claim 1 wherein obtaining a layer includes obtaining a thin layer having a thickness of between about 50 nm and about 5000 nm.

11. The method as recited in claim 10 wherein obtaining a thin layer includes obtaining a thin layer having a length of about 20000 nm and a depth of about 5000 nm.

12. The method as recited in claim 1 further comprising placing the layer in a sample holder, the holder comprising:
   a main body having first and second opposing major surfaces, a recess in the first major surface and a main body aperture narrower than the recess and extending from a base of the recess to the second major surface; and
   a plug that engages an inner wall of the recess to fix the plug with respect to the main body and fix a grid containing the sample between the base and the plug, the plug having a plug aperture extending therethrough that aligns with the main body aperture to form a path to and through the sample for a beam from a selected one of multiple analytical tools.

13. The method as recited in claim 1 further including determining a detection limit of the analytical tool and wherein preparing a calibration standard includes determining the concentration with a first analytical tool and determining a detection limit of the analytical tool includes determining a detection limit of a second analytical tool.

14. The method as recited in claim 13 wherein the first analytical tool is a secondary ion mass spectrometer and the second analytical tool is selected from the group consisting of:
   energy dispersive spectrometry (EDS),
   microcalorimetry,
   auger electron spectroscopy (AES), and
   x-ray photoelectron spectroscopy (XPS).

15. A system for calibrating an analytical tool, comprising:
   a first analytical tool capable of determining a concentration of an element located within a calibration standard;
   a focused bean apparatus;
   a layer extracted from the calibration standard with the focused beam apparatus, the layer being representative of the concentration of the element;
   a second analytical tool having a measurement limit of the element less than its concentration, the layer being used to calibrate the second analytical tool.

16. The system as recited in claim 15 wherein the first analytical tool is a secondary ion mass spectrometer (SIMS).

17. The system as recited in claim 15 wherein the calibration standard has a concentration of the element of about 1E21 atoms/cm$^3$ of the element.

18. The system as recited in claim 15 wherein the focused beam apparatus is a focused ion beam apparatus.

19. The system as recited in claim 15 wherein the second analytical tool is selected from the group consisting of:
   energy dispersive spectrometry (EDS),
   microcalorimetry,
   auger electron spectroscopy (AES), and
   x-ray photoelectron spectroscopy (XPS).

20. The system as recited in claim 15 wherein the layer is a thin layer having a thickness of between about 50 nm and about 5000 nm.

21. The system as recited in claim 20 wherein the thin layer has a length of about 20000 nm and a depth of about 5000 nm.

22. The system as recited in claim 15 wherein the second analytical tool has a sample holder bay and the system further includes a sample holder configured to hold the calibration standard and cooperatively engage the sample holder bay.

23. The system as recited in claim 22 wherein the sample holder comprises:
   a main body having first and second opposing major surfaces, a recess in the first major surface and a main body aperture narrower than the recess and extending from a base of the recess to the second major surface; and
   a plug that engages an inner wall of the recess to fix the plug with respect to the main body and fix a grid containing the sample between the base and the plug, the plug having a plug aperture extending therethrough that aligns with the main body aperture to form a path to and through the sample for a beam from a selected one of multiple second analytical tools.

* * * * *